US007527789B2

(12) United States Patent
Loibner et al.

(10) Patent No.: US 7,527,789 B2
(45) Date of Patent: May 5, 2009

(54) USE OF A PREPARATION BASED ON AN ANTIBODY DIRECTED AGAINST A TUMOR-ASSOCIATED GLYCOSYLATION

(75) Inventors: Hans Loibner, Vienna (AT); Gottfried Himmler, Vienna (AT); Thomas Putz, Innsbruck (AT); Michael Freissmuth, Vienna (AT); Markus Klinger, Vienna (AT); Hesso Farhan, Vienna (AT)

(73) Assignee: Igeneon Krebs-Immuntherapie Forschungs-Und Entwicklungs-AG, Vienna (AT)

( * ) Notice: Subject to any disclaimer, the term of this patent is extended or adjusted under 35 U.S.C. 154(b) by 389 days.

(21) Appl. No.: 10/519,323

(22) PCT Filed: Jun. 30, 2003

(86) PCT No.: PCT/EP03/06912

§ 371 (c)(1),
(2), (4) Date: Dec. 23, 2004

(87) PCT Pub. No.: WO2004/005349

PCT Pub. Date: Jan. 15, 2004

(65) Prior Publication Data

US 2005/0226880 A1    Oct. 13, 2005

(30) Foreign Application Priority Data

Jul. 3, 2002    (AT) ................................ A 995/2002

(51) Int. Cl.
*A61K 39/395*    (2006.01)
(52) U.S. Cl. .................................. 424/143.1; 530/387.1
(58) Field of Classification Search ........................ None
See application file for complete search history.

(56) References Cited

FOREIGN PATENT DOCUMENTS

| EP | 0528767 A | 2/1993 |
|---|---|---|
| WO | WO 8911288 A1 | 11/1989 |
| WO | WO 0100245 A | 1/2001 |
| WO | WO 0170268 A1 | 9/2001 |
| WO | WO 0233073 A1 | 4/2002 |
| WO | WO 02092771 A | 11/2002 |

OTHER PUBLICATIONS

Blaszczyk-Thurin.M.et.al. Molecular recognition of the lewis Y antigen monoclonal antibodies. protein Engineering.1996. 9:447-459.*
Saleh et al. Journal of Clinical Oncology, vol. 18, No. 11, pp. 2282-2292, Jun. 2000.*
Trail et al. Clinical Cancer Research, vol. 5, pp. 3632-3638, Nov. 1999.*
Basu et al. Cancer Research, vol. 47, pp. 2531-2536, May 15, 1987.*
Kumar et al. Seminars in Oncol. vol. 28 (5 Suppl. 16), p. 27-32, Oct. 2001. Abstract only.*
Alsabti et al. (J. of Cancer Res. and Clin. Oncology, vol. 95, pp. 209-220, 1979).*
Ravingerova et al. (Molecular and Cellular Biochemistry, vol. 247, pp. 127-138, May 2003).*
Dettke, M. et al.: "Different types of FCgamma-receptors are involved in anti-Lewis Y antibody induced effector functions in vitro" British Journal of Cancer, vol. 82, No. 2, Jan. 2000, pp. 441-445.
Basu, A. et al. "Presence of tumor-associated antigens in epidermal growth factor receptors from different human carcinomas" Cancer Research, vol. 47, No. 10, May 15, 1987, pp. 2531-2536.
Gooi, H.C. et al: "Monoclonal antibody (EGR/G49) reactive with the epidermal growth factor receptor of A431 cells recognizes the blood group ALeb and ALey structures" Molecular Immunology, vol. 22, No. 6, Jun. 1985, pp. 689-693.
Brich, Z. et al: "Preparation and characterization of a water soluble dextran immunoconjugate of doxorubicin and the monoclonal antibody (ABL 364)" Journal of Controlled Release, vol. 19, No. 1/3,Mar. 1, 1992, pp. 245-257.

* cited by examiner

*Primary Examiner*—Larry R. Helms
*Assistant Examiner*—Meera Natarajan
(74) *Attorney, Agent, or Firm*—Birch, Stewart, Kolasch & Birch, LLP.

(57) ABSTRACT

The invention relates to the use of a preparation based on an antibody directed against a tumor-associated glycosylation for preparing a medicament for the prophylactic and/or therapeutic treatment for the reduction or inhibition, respectively, of the growth of tumor cells in a cancer patient, as well as to a pharmaceutical preparation containing an antibody directed against a tumor-associated glycosylation. Moreover, the invention relates to a preparation for pharmaceutical and/or diagnostic use, a diagnostic method and an agent for determining the risk of metastasis formation in a cancer patient, as well as a method of producing a preparation based on a body fluid or tissue, in each case using the antibody directed against a tumor-associated glycosylation.

28 Claims, 7 Drawing Sheets

Figure 1:

U E E H H E E H H E
A   A   T IGN T IGN

Fig. 6B,C
B
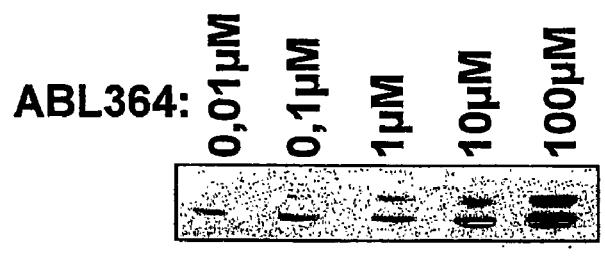
ABL364: 0,01µM 0,1µM 1µM 10µM 100µM
U ← EGF (1,6nM) →
Trastuzumab: 1nM 3nM 10nM 30nM 100nM
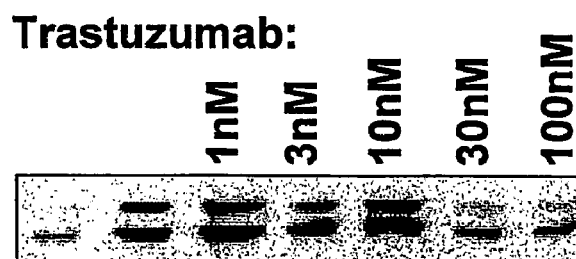
U ← EGF (1,6nM) →
C
+IGN311 +ABL364 1nM 10nM 100nM 1µM 10µM
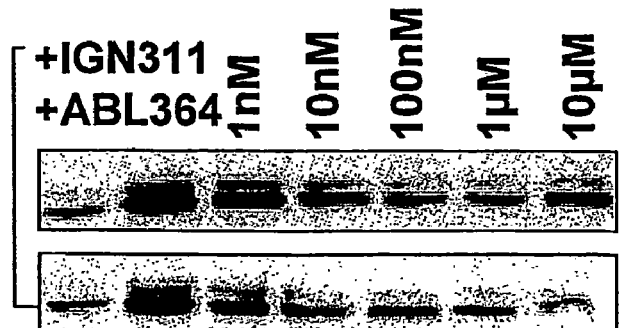
U ← EGF (1nM) →

USE OF A PREPARATION BASED ON AN ANTIBODY DIRECTED AGAINST A TUMOR-ASSOCIATED GLYCOSYLATION

The invention relates to a new use of an antibody preparation, a pharmaceutical preparation for treating cancer patients as well as a method for determining or reducing tumor cells.

The receptor for epidermal growth factors, termed ?epidermal growth factor(EGF) receptor?, is a plasma membrane glycoprotein having tyrosine-kinase activity, which is activated by binding to a ligand, e.g. of EGF or of heregulin. By binding the growth factors, the dimerisation and the trans- or auto-phosphorylation of the receptor is caused, and thus a signal cascade for cell division is initiated. After phosphorylation, the MAP kinase is activated. As mitogen-activated protein kinase (MAP-kinase), these receptors thus assume a central position in the regulation of cell growth and cell division. The two isoforms p42 and p44 of the MAP kinase are also designated erk1 and erk2.

Particularly by tumor cells MAP kinase is unproportionally highly presented, whereby the latter, or the EGF receptors, respectively, are considered as tumor-associated antigens (TAA).

Tumor-associated antigens (TAA) often form the basis for the development of immunotherapeutical agents for the prophylaxis and/or treatment of cancer. TAA are structures which preferably are expressed on the cell membrane of tumor cells, thereby enable a differentiation from non-malignant tissue and therefore can be viewed as targets for diagnostic and therapeutic applications of specific antibodies.

The unchecked growth of tumors possibly is prevented by blocking the MAP kinase. In the prior art, a number of antibodies has been described which can specifically bind to the MAP kinase, or to EGF receptors, respectively.

In WO 02/092771, specific binding members are described that bind directly to the EGFR epitope that is found in tumorigenic, hyperproliferate or abnormal cells and not detectable in normal cells.

In WO 02/33073 a modified antibody is described which transduces a signal into cells by crosslinking a cell surface molecule to serve as an agonist.

In WO 01/70268 a combination of an antibody and an agent is described wherein the agent blocks the cell cycle in the G2 or M-phase.

In these documents, the use of an antibody against aberrant tumor glycosylation is not described.

In EP 0 359 282 A, monoclonal antibodies are described which bind to the extracellular domain of the human EGF receptor. By this, the cell growth of tumor cells is to be inhibited.

An antibody directed against the "Epidermal Growth Factor" receptor-2 (HER-2) has also been used in combination with chemotherapy (Anticancer Drugs 2001, 12 Suppl 4: pp. 3-10).

A further antibody which binds to the family of EGF receptors is, e.g. described in U.S. Pat. No. 5,811,098, this antibody specifically binding to HER4, a human tyrosine kinase-receptor.

WO 96/40210 A describes chimeric or humanized variants of a certain anti-EGF-receptor antibody for inhibiting tumor growth.

The blocking of the MAP kinase by certain antibodies which are directed against the extracellular domain of the EGF receptors has the disadvantage that not only tumor cells are attacked, but any mitotically activated cell.

The treatment of cancer patients not only comprises the prevention of tumor growth, much rather also the formation of metastases is to be prevented for a longer period of time. This might be indicated after treatment of the primary tumor by surgery and/or after chemotherapy (e.g. radiotherapy) has been effected. Disseminated tumor cells may be in their dormant state and often cannot be attacked by the chemotherapy (radiotherapy). A thus treated patient seemingly is in a healed state, which is also described as "minimal residual disease". Nevertheless, the dormant tumor cells have a potential of forming metastases if they become metastasising cells due to a growth stimulus also after a longer dormant state.

In the course of discovering and subsequent characterising the most varying TAA it has been found that they have important functions for cancer cells. They allow the degenerated cells to exhibit properties characteristic of the malignant phenotype, such as, e.g., an increased adhesion capacity, which are highly important for establishing metastases. However, in certain stages, such antigens may very well be expressed on normal cells where they are responsible for normal functions of these cells. An example of this is the Lewis Y carbohydrate antigen which appears on the plurality of tumors of epithelial origin, but also plays an important role during the fetal development of epithelial tissues. It has been shown that the expression of this antigen in lung cancer is highly associated with an unfavorable prognosis, since Lewis Y positive cancer cells apparently have a higher metastatic potential (N. Engl. J. Med. 327 (1992), 14). Therefore it can be assumed that the potential for developing metastases is given by the degree of glycosylation of tumor cell receptors.

In EP 0 528 767 A, the use of a humanized anti-Lewis Y antibody for the treatment of epithelial cancer has been described.

Among the further known tumor-associated carbohydrate structures, there are, e.g., all those Lewis antigens which are increasingly expressed in many types of epithelial cancers. Among them are Lewis x-, Lewis b- and Lewis y-structures, as well as sialylated Lewis x-structures. Other carbohydrate antigens are GloboH-structures, KH1, SialylTn or Tn antigen, TF antigen, the alpha-1,3-galactosyl epitope (Elektrophoresis (1999), 20:362; Curr. Pharmaceutical Design (2000), 6:485, Neoplasma (1996), 43:285).

Tumor cells which express sialyl-Le$^a$ or di-sialyl Le$^a$ can form metastases by binding to endothelial cells with cell adhesion receptors. This binding can, e.g., be prevented according to U.S. Pat. No. 6,121,233 by incubation with carbohydrate structures, such as sialyl-Le$^a$ or di-sialyl Le$^a$.

Similarly, according to EP 0 521 692, the metastasizing potential of tumor cells is inhibited, wherein a mimic is administered selected from the group of monosialosyl-Le I, monosialosyl-Le II, disialosyl-Le and Sialosyl Le.

By using different tumor cells it has be shown that also EGF receptors have unusual carbohydrate structures, i.e. carbohydrate-TAA, such as the sialylated type Le$^x$/Y (Cancer Research 47, 2531-2536, 1987).

Direct therapeutic applications of antibodies against TAA are based on passive immunotherapies, i.e., a specific antibody is systemically administered in a suitable amount to cancer patients and exerts an immunotherapeutic action. The biologic half-life of such agents depends on their structure and is limited. Therefore, it is necessary to repeat the applications. When using xenogenic antibodies (e.g. murine monoclonal antibody, MAB), this may, however, lead to undesired immune reactions which may neutralise a possible therapeutic effect and may cause dangerous side effects (anaphylactic reactions). Therefore, such immunotherapeutic agents can be administered for a limited time only.

A better tolerance is obtained by reducing the xenogenic structures of the antibody and by introducing human structures, e.g. with chimeric or humanized antibodies. Also systems for producing specific human antibodies are developed. Thus, certain cell lines can produce human monoclonal antibodies.

The object of the invention is to improve the treatment of cancer patients by specifically suppressing the growth of tumor cells, or the metastasising potential of tumor cells.

According to the invention, this object is achieved by the subject matter of the claims.

According to the invention, a preparation based on an antibody, directed against a tumor-associated glycosylation, is used for preparing a medicament for a prophylactic and/or therapeutic treatment for reducing and inhibiting, respectively, the growth of tumor cells in a cancer patient. The inventive use particularly relates to the treatment of patients who are subjected to a chemotherapy. By binding the tumor-specific antibodies to a tumor cell, not only the tumor cell lysis becomes possible. Also all the functions of the tumor cells which are exerted via glycosylated surface receptors are suppressed. Thus, a chemotherapy can attack the cell much more effectively in combination with the inventive use. This is primarily suggested for the indication of a chemotherapy resistance. In this case, tumor cells have developed defense mechanisms which are mediated by surface receptors. A further indication is the "minimal residual disease", for which disseminated tumor cells are to be attacked.

Surprisingly it has been found that the surface receptors of a tumor cell having an aberrant glycosylation can functionally be blocked in a precise manner via antibodies against this glycosylation. This not only relates to a certain surface receptor, such as the EGF receptor family receptor, wherein the HER-2/neu (ErbB2) is an example of the family members Practically all the tumor-specific receptors which are characterized by aberrant glycosylation are simultaneously blocked. Among them are, e.g., all the receptors of the EGF receptor family, the CD55 (791Tgp72/DAF—decay accelerating factor) receptor, the transferrin receptor and the P-glycoprotein. Thus, the tumor cell is attacked on the basis of different mechanisms of action.

Surprisingly it has been found that antibodies directed against an aberrant glycosylation bind in functional manner to several receptors of the family of the EGF receptors and thus the signal cascade for inducing the cell growth can effectively be blocked. It could be demonstrated that it was possible to functionally bind in particular the erk1 and erk2 isoforms of the MAP kinase by means of the inventively used antibodies. The binding of the growth factors to the receptors was thereby prevented or reduced, respectively. This treatment is more specific as compared to immunotherapy using antibodies against the proteinaceous extracellular part of the EGF receptor, since the unusual tumor-associated carbohydrate structures are missing on the EGF receptors of normal cells. On the other hand, the treatment is more universal, since simultaneously different receptors having the same aberrant glycosylation are blocked.

By the use according to the invention, an anti-carbohydrate antibody is provided for the first time for immunotherapy and for inhibiting glycosylated tumor cell receptors, in particular for preventing the mitogenic stimulation of a cancer cell by EGF or heregulin. The mitosis of normal cells is to proceed largely undisturbed, and respective side effects are to be avoided. The specific binding of the antibodies via a tumor-associated glycosylation of cancer cells to the receptors of growth factors blocks the interaction of the latter with their physiologic ligands and inhibits the signal transduction through these receptors and thus, the cell growth. These antibodies thus are competitively functionally effective.

At the same time, such an antibody can specifically attack the tumor cell by its action within the humoral and cellular immune system. Tumor cells which express the EGF receptor or receptors of the EGF receptor family, respectively, according to the invention are specifically bound and can be lysed. These functions of the antibody are determined by its ADCC and CDC activity (ADCC: antibody-dependent cellular cytotoxicity; CDC: complement dependent cytotoxicity), which both are activities that can be determined by means of standard tests. With these functions, the inventive treatment of the cancer patients has an advantage over other competitive binding partners, e.g. the carbohydrate mimics known in the prior art which, of course, do not exhibit any antibody activities.

According to the invention, antibody preparations can be used whose active substance has both the function of the competitive binding and that of tumor cell lysis. A further aspect of the present invention, however, relates to a preparation based on a modified antibody or antibody derivative which merely blocks the MAP kinase and does not cause any lytic activity therebeyond, e.g. by none or a reduced CDC and ADCC activity, e.g. of less than 50%. Preferentially, the antibody according to the invention having reduced or no CDC and ADCC activity does not contain the Fc part or has only parts of Fc sequences. This preparation can be employed pharmaceutically and/or diagnostically. Even if the antibody activities are reduced in the preparation according to the invention, a particularly good effect can be achieved if, e.g. by a fragmentation and/or derivatization, the half life is increased.

A possible treatment objective is the effective binding and reduction of tumor cells, i.e. tumor tissue or metastases or, in particular, disseminated tumor cells. The number of tumor cells, or micrometastases, respectively, detectable in blood, bone marrow or organs shall be significantly reduced. The formation of metastases is to be retarded, their growth is at least to be slowed down. Thus, the relapse-free life span and thus also the total survival time of the patients can be lengthened by the specially targeted immunotherapy.

Within the scope of the use according to the invention, in particular the treatment for reducing, or inhibiting, respectively, the growth of tumor cells in a cancer patient, also a hemodialysis is possible. However, also body fluids or tissues, such as skin or other organs, which have been derived from a donor who has the risk of a cancer disease may prophylactically be treated ex vivo with the antibody directed against a tumor-associated glycosylation. A possible risk of a transmission of tumor cells by a contaminated donation is minimized.

Cancer patients who are subjected to a high dosage chemotherapy often are bone marrow donors or donors of hematogenic stem cells which they receive again for an autotherapy, after the chemotherapy has been effected. It is exactly this material which possibly is contaminated with tumor cells, and it is particularly used for the treatment according to the invention. After the high dosage therapy, the patient can then receive the preparation which has been decontaminated according to the invention. The method of ex vivo treatment of bone marrow cells or blood cells with various methods like treatment with chemotherapeutic agents or radiotherapy is known as "purging". It is attempted to avoid the contamination with metastases by these treatments (Semin Oncol 1999, 26(2), 545-51; Hematol Oncol Clin North Am 1993, 7(3), 687-715).

According to the invention, also a method of producing a preparation based on a body fluid or tissue is provided, which provides for the ex vivo treatment of the body fluid or of the tissue with an antibody directed against a tumor-associated glycosylation so as to form a cellular immune complex, and optionally separation of the immune complex from the body fluid. The obtainable preparation has a substantially reduced risk of having a tumor content, and a reduced metastasis-forming potential, respectively, and it is primarily characterised by a reduced content of receptors of the EGF receptor family.

The material treated according to the invention ex vivo in particular is derived from bone marrow, blood, serum or organ components of a patient or donor. After having been treated with the specific antibody, optionally an appropriate immune complex has been formed which then is optionally comprised together with the material, and with the specific antibody, respectively, in a preparation ready for administration. For, if the material contains tumor cells, the latter are recognized and bound by the antibody. From this there results a cellular immune complex of the antibody with a tumor cell or with cellular components of a tumor cell. This immune complex may remain in the material, yet preferably it is separated from the material. For this, in particular a solid or liquid carrier is used which localizes the immune complex. By separating the carrier from the treated material, the immune complex can be separated. According to a particularly preferred embodiment, the antibody is immobilized on a solid carrier already prior to the treatment, the body fluid or a rinsing liquid of the tissue is incubated with the carrier, and the treated fluid or liquid is separated from the carrier.

An equal method is also suitable for the inventive determination of a metastasis-forming potential in a sample from a patient. According to the invention, the risk of metastasis formation is determined by the qualitative and/or quantitative determination of tumor cells as a measure for the metastasis-forming potential. In doing so, a sample of a body fluid from a cancer patient is provided which is contacted with an antibody directed against a tumor-associated glycosylation. With this, a cellular immune complex of potentially present tumor cells is to be formed with the antibody which is qualitatively and/or quantitatively determined. A diagnostic agent provided therefor contains either the antibody in combination with a carrier for separating a cellular immune complex, or in combination with a labelling for determining a cellular immune complex. Preferably, the antibody is labelled by conjugation with an enzyme, a radioactive component or another detecting agent.

According to the invention, the treatment of patients with tumor cells with aberrant glycosylation becomes possible, e.g. tumor cells having a receptor from the EGF receptor family, or Lewis y-positive tumor cells. The preferably treated types of cancer are epithelial cancer, such as breast cancer, cancer of the stomach and intestines, the prostate, pancreas, ovaries and the lungs, but also special types of leukemia. Patients with primary tumors can be treated just as patients with secondary tumors.

The inventive treatment for the immunotherapy of cancer patients preferably is effected after resection of tumor tissue, or after chemotherapy has been effected, respectively. Preferably, the treatment is started within 1 to 2 weeks after chemotherapy.

According to the invention, primarily antibodies are used which are directed against an aberrant glycosylation of tumor cells and their receptors for growth factors. Preferred antibodies are selected from the group of antibodies which are specific of one or several of Lewis antigen structures, like Lewis x-, Lewis b- and Lewis y-structures, optionally their sialylated forms, as well as GloboH, KH1, Tn antigen, SialylTn, TF antigen and alpha-1,3-galactosyl-epitope, but also Sialyl $Le^a$ or disialyl $Le^a$, monosialosyl-Le I, monosialosyl-Le II, disialosyl-Le and sialosyl Le.

By the term "antibody", antibodies of all types are to be understood, in particular monospecific or polyspecific, monoclonal antibodies, or also chemically, biochemically or molecular-biologically prepared antibodies.

Even though the medicament according to the invention may contain a native antibody which possibly has been isolated from a cell line, an organism or a patient, often an antibody-derivative is used which is capable of specifically binding to the aberrant glycosylation. Preferably, the antibody derivative is selected from the group of the antibody fragments, conjugates or homologues, but also complexes and adsorbates. It is further preferred that the antibody derivative contains at least parts of the Fab fragment, e.g. together with at least parts of the $F(ab')_2$ fragment, and/or parts of the hinge-region and/or of the Fc portion of a lambda or kappa antibody. Furthermore, also a single-chain antibody derivative, e.g. a so-called single-chain antibody, can be employed in a vaccine as defined by the invention. Preferably, an antibody of the type of an immunoglobulin, such as an IgG, IgM or IgA, is employed.

The treatment according to the invention is specifically targeted at the tumor cells. Therefore, no side-effects are expected due to non-specific interactions. Therefore, no unproportional reactions shall be caused, even if the inventively used active substance has been derived from a non-human species, such as, e.g., a murine antibody. It is, however, assumed that a recombinant, chimeric as well as an antibody combined with human components, a humanised or human antibody, is particularly well tolerable for the administration to humans.

The binding of the antibody to at least one of the family of the EGF receptors, or to more or all receptors from the family of the EGF receptors, or to other glycosylated receptors of the cancer cell usually occurs with high affinity, or high avidity, respectively. The binding of the growth factors, or ligands, respectively, to the receptors is not only inhibited or reduced for the prophylactic treatment. The growth factors, or ligands, respectively, can also be displaced by their receptors. Accordingly, a therapeutic treatment of the tumor growth and of metastasising cancer is feasible. The preferred affinity of the antibody is below a Kd value of $10^{-6}$ mol/l, preferably less than $10^{-7}$ mol/l, most preferred $10^{-8}$ mol/l or less.

The selected antibody interferes with the binding of growth factors or other ligands to a tumor cell, preferably in a manner that the binding site for the antibody is in the vicinity, overlapping with or equal to the binding site for the growth factors, or the ligands, respectively.

For binding all the glycosylated receptors of a tumor cell, usually a high dose of at least 50 mg, preferably at least 100 mg, most preferred at least 200 mg per patient is administered. The maximum dose will depend on the tolerability of the antibody, humanized antibodies, and human antibodies, respectively, being best tolerated. A dose of up to 1 g or in some instances up to 2 g per patient and treatment may very well be advantageous. The treatment preferably is repeated at certain time intervals, according to the half life of the antibody used, which usually is in the range of from 3 to 30 days. By particularly derivatizing the antibody it is possible to increase the half life to up to several months and to thereby lengthen the treatment intervals accordingly.

The medicament used according to the invention preferably is provided in a suitable formulation. Preferred are such formulations with a pharmaceutically acceptable carrier. The latter comprises, e.g., auxiliary agents, buffers, salts and preservatives. Preferably, a ready infusion solution is provided.

Since an antibody is relatively stable, medicaments based on antibodies or their derivatives have the substantial advantage that they can be put on the market as a storage-stable solution, or as a formulation in a ready-to-use form. The former preferably is storage-stable in the formulation at refrigerator temperatures up to room temperature. The medicament used according to the invention may, however, also be provided in frozen or lyophilized form which may be thawed or reconstituted when required.

The concentration of the active substance of the medicament will depend on its tolerability. A particularly well tolerable preparation based on a humanized antibody can be administered directly to the patient at a high concentration without further dilution. By the preferred concentration in the range of from 0.1% to 10%, preferably from 1% to 5%, it is possible to keep low the administered volume and the corresponding time of infusion.

Usually, the medicament will be administered i.v. Likewise, however, also another parenteral or mucosal mode of administration can be chosen, which brings the active substance to a systemic or local application at the site of the tumor or of the metastases.

The following example as well as the figures shall explain the present invention in more detail, without, however, restricting it:

FIG. 1 shows the inhibition by IGN311, anti-ErbB1 2C225 and trastuzumab (Herceptin) of EGF- and heregulin-dependent MAPK phosphorylation in SKBR-3 cells. Quiescent cells were incubated in the absence or presence of 100 nM IGN311 (IGN), 100 nM trastuzumab (T), 30 nM 2C225 (A). Subsequently, the cells were incubated with 1 nM EGF (E), heregulin (H) or for 5 min; the extent of MAPK phosphorylation was determined by immunoblotting with an antiserum that specifically recognizes phospho-erk as outlined under "Material and Methods".

Figure 2:
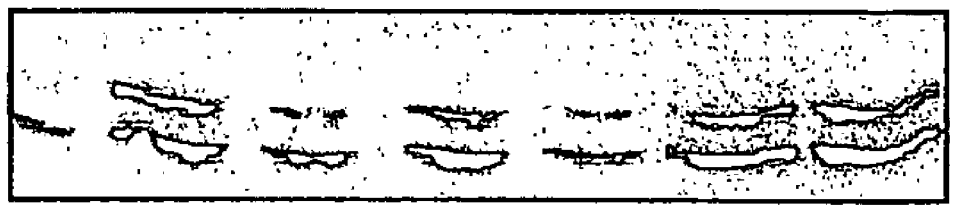

FIG. 2 shows the heat instability of the IGN311 induced inhibition of the MAP kinase stimulation (IGN311 was inactivated by heat denaturing (10 min at 95° C.). Growth-arrested SKBR3-cells were pre-incubated for 15 min with IGN311 (with IGN denoted lanes), or with heat-denatured IGN311 (with IGN* denoted lanes) or with anti-EGF-receptor antibody (with A denoted lanes). Then the cells were stimulated with EGF (with E denoted lanes); lane U corresponds to the blank value (=unstimulated cells)).

Figure 3:
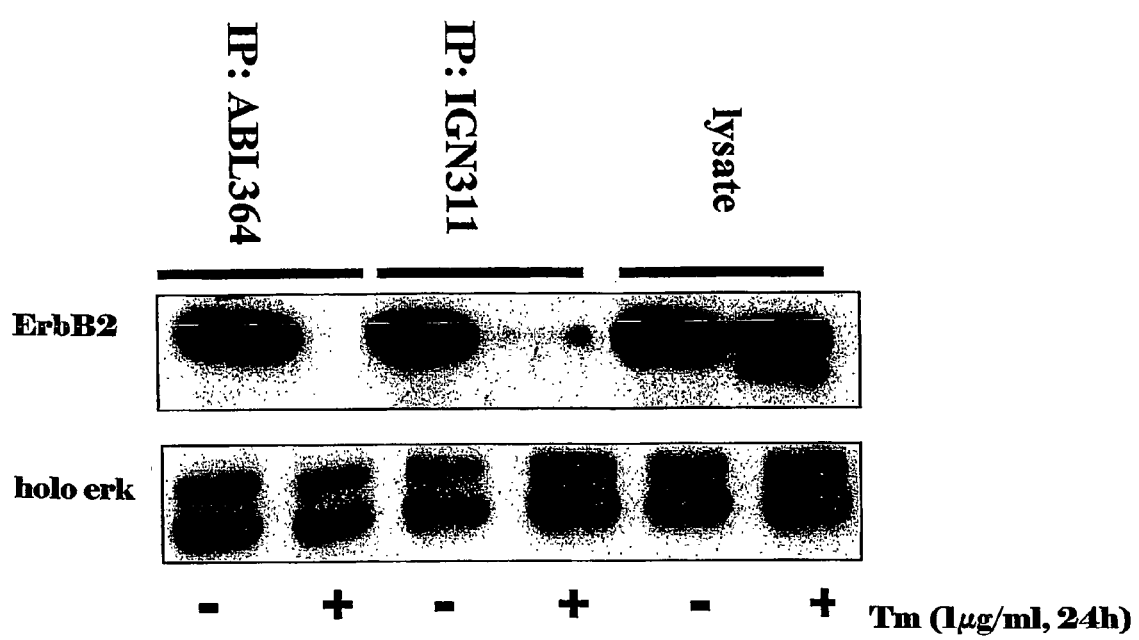

FIG. 3. shows the immunoprecipitation by IGN311 and ABL364 of erbB2 from tunicamycin-treated (TM) and control SKBR-3 cells. The data show that binding of the antibody according to the invention only occurs when the protein is glycosylated and when modified Lewis y antigen is localized on the surface of the molecule.

Figure 4:
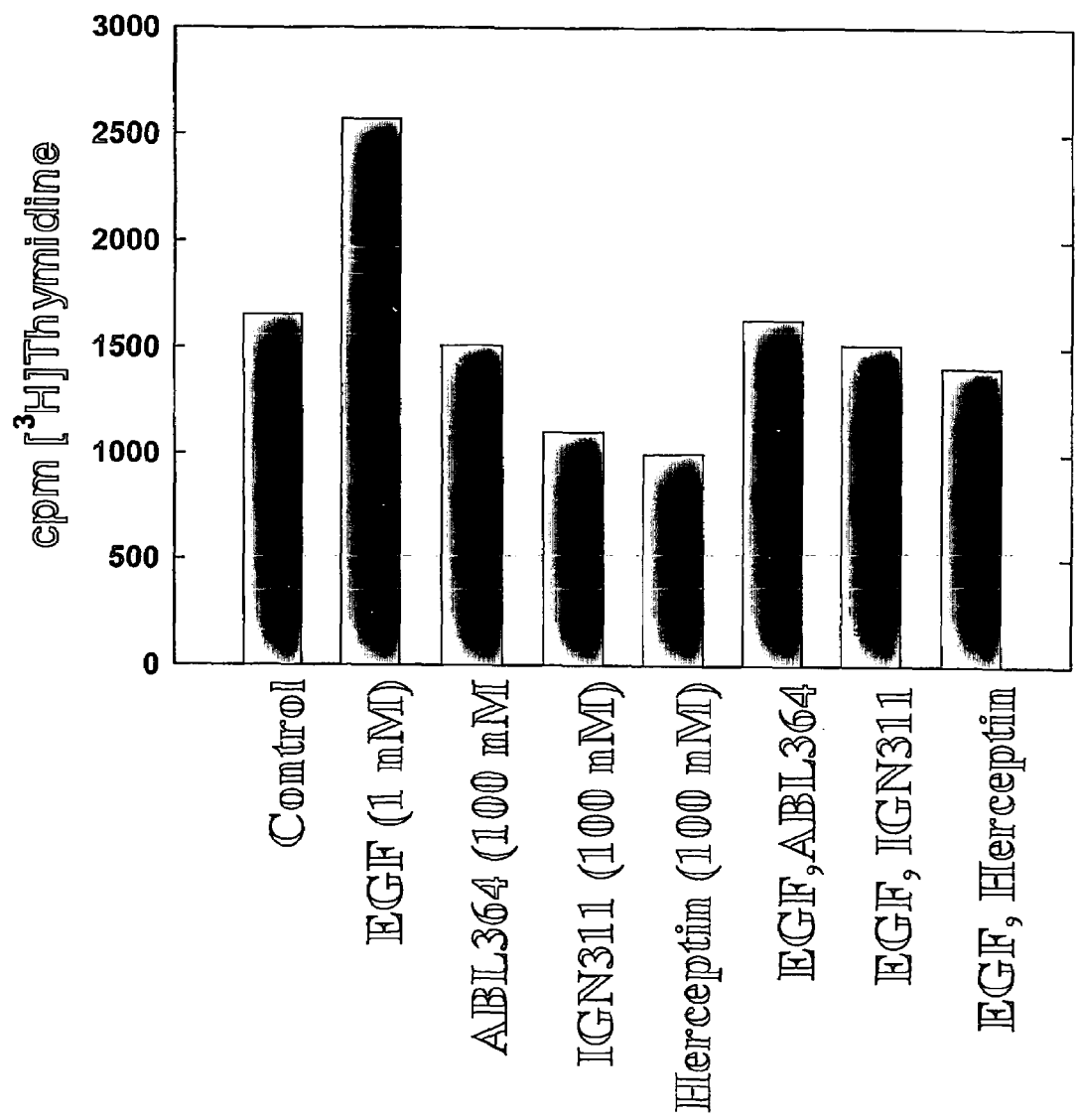
Figure 5:
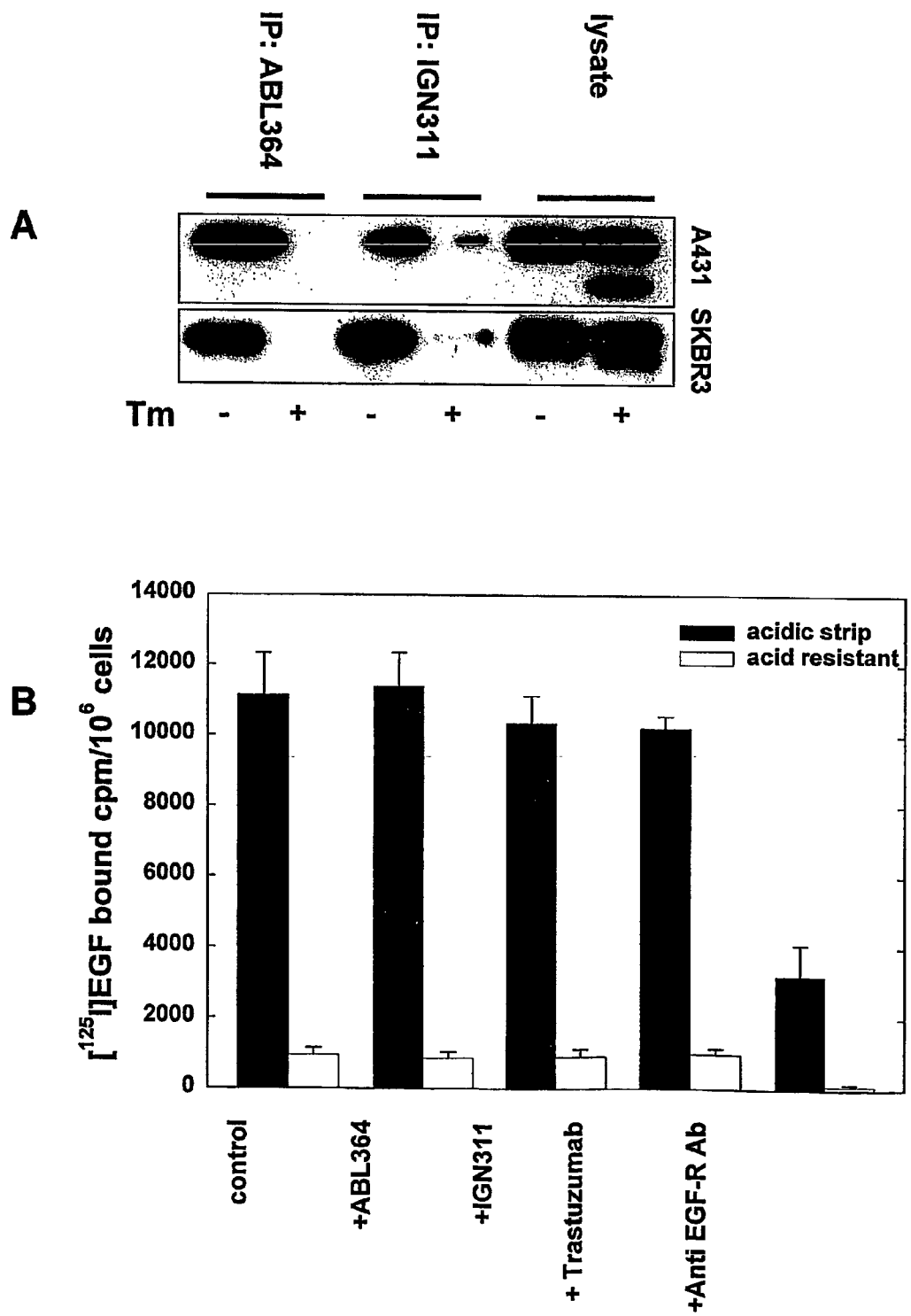

FIG. 4 shows the EGF-stimulated [$^3$H]thymidine incorporation in SKBR-3 cells in the presence of ABL364, IGN311 or herceptin. The binding of growth factors to their receptors is blocked by the antibodies according to the invention and additionally, the growth of the tumor cell and its capability for dividing is at least reduced or completely blocked FIG. 5. Panel A: Immunoprecipitation of ErbB1 and ErbB2 from A431- and SKBR-3 cells by IGN311 and ABL364. Confluent A431- and SKBR-3 cells were incubated in the presence (+) or absence (−) of 1 µg/ml tunicamycin (Tm) for 24 h. Cell lysates were prepared and LeY-modified proteins were immunoprecipitated by the addition of IGN311 or ABL364 as indicated. Aliquots (30%) of the immunoprecipitate were loaded onto SDS-polyacrylamide gels. Immunoblotting was performed with antibodies recognizing ErbB1 (A431 cell lysate, upper blot) and ErbB2 (SKBR-3, lower blot). Data are from a representative experiment that was reproduced twice. Panel B: Binding of [$^{125}$I]EGF to intact SKBR-3 cells in the absence or presence of ABL364, IGN311 or trastuzumab. SKBR-3 cells were incubated in medium containing 1 nM [$^{125}$I]EGF in the absence or presence of 10 nM 2C225, 100 nM ABL364, 100 nM IGN311 or 100 nM trastuzumab at 4° C. (to prevent internalization) for 60 min. The binding reaction was terminated and surface bound and internalized [$^{125}$I]EGF was determined as described under "Material and Methods".

FIG. 6. Panel A: Concentration-dependent stimulation of MAPK phosphorylation by EGF in the absence and presence of ABL364, IGN311 and anti-EGF-receptor antibody 2C225. Quiescent SKBR-3 were preincubated with vehicle (upper blot) or in the presence of 100 mM mABL364, 100 nM IGN311 or 30 nM 2C225 (as indicated, lower blot) and subsequently stimulated with increasing concentrations of EGF. Panels B&C: Concentration-dependent inhibition by ABL364, IGN311 and trastuzumab of the EGF- or heregulin-induced stimulation of MAPK (B,C). Panel B: Quiescent SKBR-3 cells were incubated in the presence of increasing concentrations of ABL364 or trastuzumab. Thereafter cells were stimulated with 1.6 nM EGF. Panel C: Quiescent A431 cells were incubated in the presence of increasing concentrations of mABL364 or IGN311 and thereafter stimulated with 1 nM EGF. The extent of MAPK phosphorylation was determined as described in "Material and Methods".

EXAMPLES

Materials and Methods:

Materials. A431 and SKBR-3 cell lines were from ATCC (Manassas, Va.). [$^{125}$I]EGF was from Perkin Elmer Life Science NEN (Boston, Mass.). EGF was from Oncogene Research Products (San Diego, Calif.). Heregulin β-1 and the anti EGF-receptor antibody (Ab-2, clone 225) were from NeoMarkers (Fremont, Calif.). The anti-Lewis antibody ABL364 was obtained from Novartis (CH); its humanized version IGN311 (10) was produced for Igeneon under GMP conditions by BioInvent (Lund S) Trastuzumab (Herceptin®) was from Roche (CH). The antibody directed against the diphosphorylated sequence of erk1 and erk2 and antibodies recognizing ErbB1 and ErbB2 were from Cell Signaling Technologies Inc. (Beverly, Mass., USA). SuperFect® polycationic transfection reagent and plasmid preparation kits were from Qiagen (Hilden, FRG). The antibody recognising the carboxy terminus of erk1/erk2 was from Santa Cruz (Santa Cruz, Calif.). Fluorescence imaging was done using a Zeiss Axiovert 200M inverted epifluorecence microscope equipped with a CoolSNAP fx cooled CCD camera from Photometrics, Roper Scientific (Tucson, Ariz.). The fluorescence filter sets were from Chroma Technology Corp. (Brattleboro, Vt.). Fluorescence imaging software was from MetaSeries software, Universal Imaging Corp. (Downington, Pa.). In order to generate a CFP-tagged H-Ras, h-ras cDNA (in pcDNA3) was subcloned into pECFP-C1 (Clontech, Palo Alto, Calif.) with Kpn I and Apa. I. The plasmid coding for H-Ras was a generous gift from Martina Schmidt, the sources for the other plasmids and reagents employed are listed elsewhere (12). Cell culture. SKBR-3 and A431 cells were propagated in McCoy's modified medium and Dulbecco's modified Eagle medium (DMEM), respectively, containing 10% FCS, antibiotics and glutamine.

Stimulation of MAPK Assay, Immunoprecipitation and Immunoblotting. Following a 24 h period if cells were transfected with plasmid DNA, cell layers (70-90% confluence) were rendered quiescent by serum starvation for 12 h. Cells were subsequently stimulated by addition of medium containing or lacking agonists and maintained at 37° C. for five minutes; antibodies were added 15 min before stimulation with agonists in MAPK assays. The exposure to agonists or vehicle was terminated by rapid rinsing with ice-cold phosphate-buffered saline; thereafter, the dish was immediately immersed in liquid nitrogen; after rapid thawing, cells were lysed by addition of 80 μl lysis buffer described in J. Bio. Chem. (2002), 277, 32490-32497. The cellular debris was removed by centrifugation at 10,00×g for 10 min. Aliquots of the supernatant corresponding to 10-30 μg protein were dissolved in Laemmli sample buffer and applied to SDS-polyacrylamide gels. Immunoblotting was done as described in (J. Bio. Chem. (2002), 277, 32490-32497). For immunoprecipitating HA-GFP-tagged MAPK, the anti-HA antibody 16B12, precoupled to protein G-sepharose was used.

Preparing cell lysates for immunoprecipitation of ErbB. Cell lysates were prepared in a manner similar to that described for MAPK assay in a different lysis buffer (in mM: 20 Tris, 150 NaCl, 1 EDTA, 1 EGTA, 1 $Na_3VO_4$, 40 β-glycerophosphate, 1 PMSF, 10 NaF, pH adjusted to 7.5 with HCl; 1% triton X-100, 250 U/ml aprotinin, 40 μg/μl leupeptin). For immunoprecipitation cellular lysates (500 μg) were incubated with ABL364 or IGN311 (each at 20 μg per individual sample), precoupled to protein G-sepharose. Immunoblotting for ErbB-receptors was done as outlined in, using the appropiate antibodies.

[$^{125}$I]EGF binding to intact cells, internalization assay. Cells were resuspended in culture medium containing 0.1% FCS and 10 mM Hepes.NaOH, pH 7.5 ($5*10^5$-$10^6$ cells/assay). Subsequently the appropriate antibody was added and after 15 min the reaction was started by adding 1 nM [$^{125}$I] EGF (specific activity 900 cpm/fmol). The experimental approach is based on the assay described in ref. (13). In brief, to prevent internalization, the reaction was incubated at 4° C. After the [$^{125}$I]EGF reached equilibrium (i.e. 60 min), the reaction was split into the individual samples which were incubated for the time indicated at 37° C. Internalization was stopped by immediately sedimenting the cells through ice-cold FCS at 500×g for 5 min. Subsequently, the cell pellets were resuspended in the acidic stripping buffer (150 mM acetic acid, pH 2.7, 150 mM NaCl) and incubated on ice for 10 min. Following centrifugation at 500×g for 5 min, the radioligand that was released into the supernatant by the acid stripping was defined as the cell surface-associated ligand; radioactivity that remained within the cells after the acidic strip was defined as the internalized ligand. The cell pellets were solubilized in 100 mM NaOH solution containing 0.1% SDS and counted for radioactivity. If solely [$^{125}$I]EGF binding to intact cells was to be determined, the cells were maintained at 4° C. for 60 min and the reaction was terminated by sedimenting the cells through ice-cold FCS at 500×g for 5 min.

[$^{125}$I]EGF recycling assay. The preparation of cells, the binding buffer and the concentration of [$^{125}$I]EGF were the same as outlined above. The binding reaction was done at 37° C. for 60 min to allow for internalization. Subsequently the cells were sedimented twice through ice-cold FCS at 500×g for 5 min to remove unbound [$^{125}$I]EGF. The cell pellets were resuspended in binding buffer devoid of [125I]EGF in the absence or presence of the individual antibody, split into the individual samples and incubated at 37° C. for the time indicated. Recycling of ErbBs was stopped by immediately sedimenting the cells through ice cold FCS at 500×g for 5 min. The radioligand appearing in the supernatant represented the recycled [$^{125}$I]EGF. The subsequent acidic strip and further steps were done as outlined above.

Fluorescence microscopy-imaging of CFP tagged Ras and Oregon-Green-modified EGF in SKBR-3 cells. SKBR-3 cells were seeded onto poly-D-lysine coated glass coverslips. After 24 h, the cells were maintained under starving conditions for 12 h. If CFP-Ras was visualized, the cells were treated with 1 nM EGF for 15 min at 37° C. For imaging Oregon-Green—modified EGF, the medium was changed against PBS lacking or containing 100 nM ABL364 or IGN311 if indicated and following a 15 min incubation at 37° C., 20 nM Oregon-Green-modified EGF was added. Subsequently, the cells were maintained at 37° C. for 15 min and the unbound fluorescent EGF was removed by 3 washes with PBS. Imaging was done with a 63× oil immersion objective using a filter set allowing for excitation at 500 nm and for recording of emission at 535 nm. The pictures were captured with a CCD-camera, stored in digitized form and processed with MetaSeries software (release 4.6; MetaFluor and MetaMorph; Universal Imaging Corp., Downington; PA).

Example I

Inhibition of the Growth Factor-mediated Stimulation by the Human Anti-Lewis Y-antibody IGN311

IGN311 Decreases EGF-dependent MAPK Phosphorylation

ErbB-receptors control a signalling cascade that leads to the stimulation of MAPK reviewed in Cell (1990), 61, 203-212. Activation of MAPK is achieved via dual phosphorylation (on a threonine and a tyrosine residue) by the upstream kinase Mek1. This can be monitored by employing an antiserum that is specifically directed against the dually phosphorylated MAPK. SKBR-3 cells were rendered quiescent by serum-starvation and maintained in the absence of serum. Under these conditions, MAPK was phosphorylated only to a very modest extent (FIGS. 1 and 2, lanes "U"). The cells were stimulated for 5 min by EGF (FIG. 1, lanes labeled "E") or by heregulin (FIG. 1, lanes labeled "H") in the absence and presence of IGN311, trastuzumab (Herceptin) and the anti-ErbB1 antibody 2C225 (FIG. 1, lanes labeled IGN, T and A, in the bottom row, respectively). Addition of EGF and heregulin increased MAPK phosphorylation (FIG. 1, lanes labeled "E" and "H", respectively). IGN311 decreased the response to both, EGF and heregulin; this was also true for trastuzumab and the 2C225 antibody. Thus, the ErbB1-specific antibody was capable of interfering with the response to the ErbB3-specific ligand heregulin. Similarly, trastuzumab inhibited signalling in response to heregulin and EGF (the ErbB1-specific agonist). These findings suggest that in SKBR-3-cells agonist-stimulation induces the formation of heteromeric complexes of ErbB-receptors. Furthermore, these data strongly suggest that the humanized anti-LeY-antibody IGN311 is capable of inhibiting signalling via ErbB-family members.

In order to verify that the action of IGN311 was specific, the antibody was heat-denatured; addition of boiled IGN311 (indicated by IGN* in FIG. 2) did not blunt the stimulatory effect of EGF (cf lanes E+IGN and E+IGN* in FIG. 2). An additional control consisted of SKBR-3-cells that were stimulated with the phorbol ester B-phorbol 12,13-dibutyrate (FIG. 2, lanes labeled P). In phorbol ester-stimulated cells there was no difference between MAPK phosphorylation in the presence of active or of boiled IGN311. Phorbol esters activate protein kinase C-isoforms which also stimulate MAPK phosphorylation by an action on the upstream kinases (presumably Raf-1). Because phorbol esters have an intracellular site of action, IGN311 is not expected to affect stimulation by the phorbol ester, regardless of whether it is added in the active or inactive (heat-denatured) form. Taken together, these results do not only prove that the action of IGN311 was specific, they also rule out the presence of a low molecular weight contaminant (which might have acted by interfering with MAPK activation via an intracellular site of action, e.g. on Mek1).

Example II

Inhibition of EGF-Receptor Dependent Signalling by IGN 311 and ABL364 (Murine Precursor anti-Lewis Y-antibody)

Immunoprecipitation by IGN311 and ABL364 of Glycosylated and Deglycosylated erbB2

The antibiotic tunicamycin inhibits the synthesis of dolicholphosphate-linked oligosaccharide precursor and thus inhibits N-linked glycosylation in the endoplasmic reticulum. In the absence of core glycosylation, the Lewis-Y-antigen (a difucosyl-lactosamine-glycoside moiety) cannot be added as a side chain. However, although N-linked glycosylation is cotranslational, in many instances the deglycosylated full length protein is still synthesized and this has also been demonstrated for erbB-family members (Proc. Natl. Acad. Sci. U.S.A., 1993, 90, 2900-2904) Thus, tunicamycin was employed to investigate the ability of IGN311 and of ABL364 to recognize erbB-family members. SKBR3-cells, which express abundant amounts of erbB2, were treated for 24 h with tunicamycin. This treatment altered the mobility of erbB2 (FIG. 3, right hand lane labelled lysate) but did not cause a decline in the amount of protein (FIG. 3, cf. second lane from right and right hand lane). Detergent lysates were generated from tunicamycin-treated and untreated control cells and used as input for immunoprecipitation with either ABL364 (FIG. 3, first two lanes labelled ABL364) or IGN311 (FIG. 3, lanes 3 & 4 labelled IGN311). The amount of immunoprecipitated erbB2 was assessed by blotting for erbB2. Pretreatment with tunicamycin greatly reduced the ability of the antibodies to immunoprecipitate erbB2. This indicates that IGN311 and ABL364 recognize erbB2 only, if the protein is glycosylated and—by inference based on the known specificity of the antibodies for the difucosyl-lactosamine-glycoside moiety—modified by Lewis-y antigen.

Inhibition of [$^3$H]thymidine incorporation: In order to assess the relevance of antibody-mediated MAP-kinase inhibition for growth control, SKBR3-cells were maintained for the length of a cell cycle in the presence and absence of EGF and of ABL364, IGN311 or herceptin. FIG. 4 shows the results of EGF-stimulated [$^3$H]thymidine incorporation in SKBR-3 cells in the presence of ABL364, IGN311 or herceptin. SKBR-3 cells were incubated in 5% FCS lacking ("control") or containing 1 nM EGF for 20 h. ABL364, IGN311 or herceptin (each at 100 nM) were applied with or without 1 nM EGF for 20 h. Thereafter [$^3$H]thymidine (1 µCi/ml) was added to the medium. After 4 h, the cells were frozen at −80° C. Filtration was done as indicated in "Materials and Methods". It was clearly shown that in the presence of the antibody according to the invention the incorporation of thymidin was reduced which indicates that the growth rate of the tumor cells was inhibited. The EGF induced stimulation was blocked by the antibody.

The three antibodies had a modest effect on basal (i.e. FCS-dependent [$^3$H]thymidine incorporation) with a maximum inhibition of 30% observed with herceptin. In contrast, the EGF-induced stimulation was blocked by the three antibodies.

These data show that binding of the antibody according to the invention only occurs when the protein is glycosylated and has modified Lewis y antigen on the surface.

IGN311 and ABL364 do not Inhibit [$^{125}$I]EGF Binding to Intact Cells

To examine whether binding of IGN311 and ABL364 to (LeY modified) ErbB1 interferes with the interaction of its cognate ligand, [$^{125}$I]EGF binding on intact SKBR-3 cells was measured. As can be seen in FIG. 5B, neither ABL364 nor IGN311 reduce binding of [$^{125}$.]EGF to intact SKBR-3 cells (filled bar; acidic wash). The same was true for trastuzumab (Herceptin). This was to be expected since trastuzumab binds to a domain of ErbB2 in the vicinity of the plasma membrane (Nature (2003), 421, 756-760). The binding reaction was allowed to proceed at 4° C. to prevent activation of the endocytotic machinery. Accordingly, the amount of internalized [$^{125}$I]EGF (open bar; acid resistant) was negligible. If membrane preparations of SKBR-3 and A431 cells were used in [$^{125}$I]EGF binding assays, again neither IGN311, ABL364 nor trastuzumab decreased [$^{125}$I]EGF binding (data not shown). Consistent with its ability to bind to the EGF-binding domain of ErbB1, the anti-ErbB1 antibody 2C225 substantially reduces [$^{125}$I]EGF binding to cells (right handed filled bar) as well as to A431 and SKBR-3 membranes (not shown). It is worth pointing out that the concentration of [$^{125}$I]EGF was ~1 nM, i.e. in the range of the EGF concentration used in the MAPK assays where IGN311 and trastuzumab blunted the response to EGF (see below).

Figure 6A:
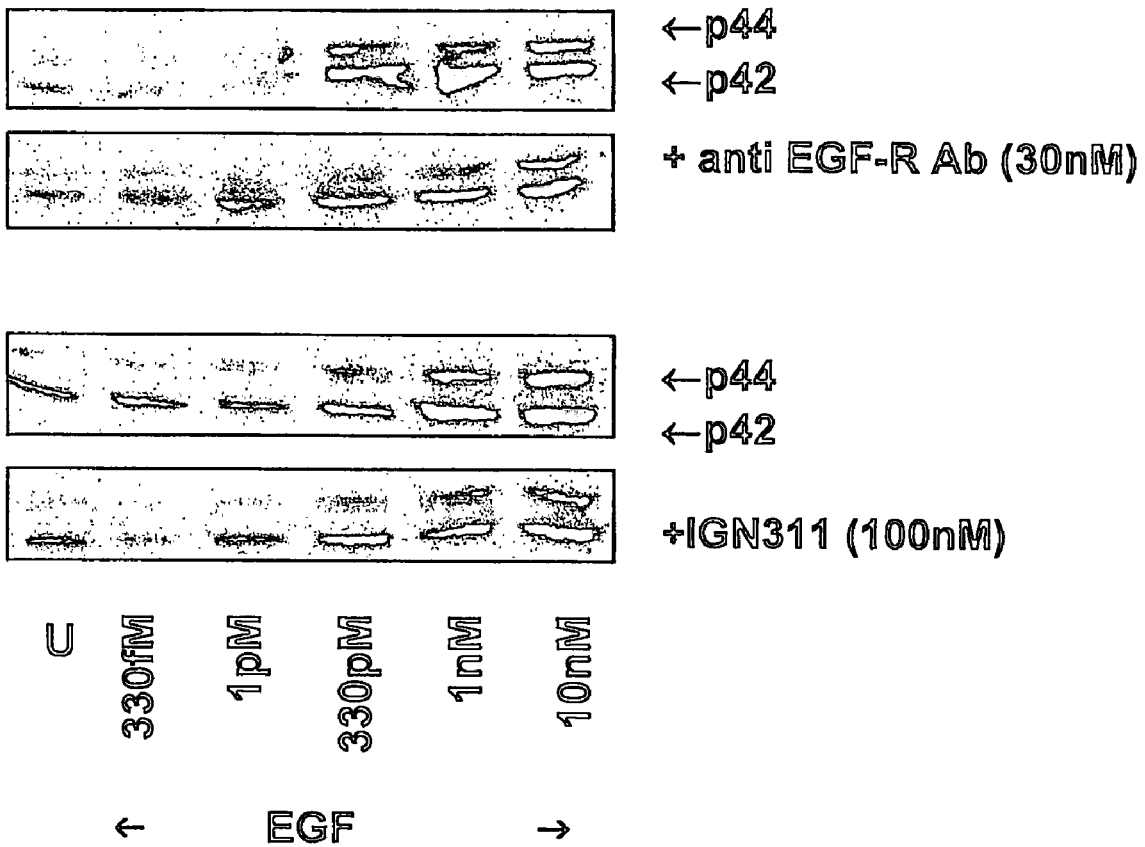

IGN311 and ABL364 Antagonize EGF-dependent MAPK Stimulation in a Non-competitive Manner ABL364 and IGN311 did not compete for [$^{125}$I]EGF binding (see FIG. 5B). Nevertheless, these antibodies inhibited EGF-dependent MAPK stimulation; thus, the action of the antibodies ought to be due to non-competitive inhibition. To verify this interpretation, the concentration-dependent effect of EGF was determined in the absence and presence of the appropriate antibodies. ABL364 and IGN311 predominantly reduced the maximum effect of EGF (FIG. 6A, middle and bottom blot). This indicates a non-competitive inhibition of EGF stimulated MAPK phosphorylation. The anti-EGF-receptor antibody 2C225 prevents binding of EGF to ErbB1 (see also FIG. 5A); because the mechanism of action of this antibody is well understood, it was used as a reference. Addition of antibody 2C225 shifted the concentration-response curve for EGF-induced stimulation of MAPK phosphorylation to the right and a maximum effect was not reached at the highest concentration of EGF employed (FIG. 6A, top).

In FIG. 6B, the cells were stimulated with a fixed concentration of EGF and the concentrations of ABL364 (FIG. 6B, left) and of trastuzumab (FIG. 6B, right) were varied. It is evident that ABL364 inhibited (FIG. 6B, left) the heregulin- and EGF-induced MAPK phosphorylation at concentrations that were in the low nanomolar range and thus consistent with its high-affinity for its cognate epitope. However, at concentrations of ≧1 µM the inhibitory action was lost and the stimulation actually exceeded that elicited by the sole addition of EGF or of heregulin. If cells were only challenged by the sole addition of ABL364 (blot at the top of FIG. 6B), the antibody was per se capable of eliciting a response at concentrations equaling or exceeding 1 µM. This may be due to the fact that ABL364 is an IgG3-isotype, which tends to aggregate; at higher concentrations, ABL364 may thus cross-link ErbB-receptors and thus favour the active state. In contrast, IGN311 did not cause stimulation even at very high concentrations (up to 5 µM; not shown) and this may be related to the fact that IGN311 is an IgG1-isotype.

Trastuzumab served as a useful comparison; its mechanism of action is distinct of that of ABL364 and of IGN311: trastuzumab specifically targets ErbB2 and it does not block binding of EGF (see also above). Trastuzumab blocked MAP-kinase stimulation by EGF in a concentration range that was certainly not lower than that of ABL364. In fact at 10 nM the extent of inhibition by the two antibodies was reasonably comparable (cf. FIG. 6B left and right).

There is no major difference in the affinity of ABL364 and of IGN311 for their cognate epitope (Cancer Res (1996), 56, 1118-1125). Thus, if their inhibitory action were related to binding to LeY antigen-modified growth factor receptors, half-maximum inhibition of MAPK stimulation ought to occur over a similar concentration range. This was the case; for both antibodies the $IC_{50}$ was estimated in the range of 3 to 10 nM (FIG. 6C). It is also worth noting that the experiment shown in FIG. 6C was done in A431 cells (in which ErbB1 is overexpressed and represents the predominant ErbB isoform). Thus, the action of ABL364 and IGN311 is not restricted to breast cancer cells.

IGN311 and ABL364 Alter the Recycling Kinetics of EGF-receptors

In many instances, receptor-dependent stimulation of MAPK is dependent on endocytosis of the agonist-liganded receptor and this reaction requires the GTPase dynamin. We verified that endocytosis was important for stimulation of MAPK by cotransfecting SKBR-3 cells with plasmids encoding wild type dynamin or the dominant negative version (GTPase deficient) of dynamin (dynamin K44A) and an epitope-tagged reporter MAPK. EGF failed to stimulate the reporter MAPK if cells expressed dominant negative dynamin K44A, but a robust stimulation was seen by fluorescence microscopy in cells expressing wild type dynamin. As an internal control (for cell viability and loading), we determined EGF-stimulated phosphorylation of endogenous MAPK. The response did not differ in lysates prepared from cells exposed to the plasmids encoding wild type or mutated dynamin; this was to be expected due to the low transfection efficiency in SKBR-3 cells (~5%).

The experiment showed that dynamin-dependent endocytosis was a prerequisite for MAPK stimulation in SKBR-3 cells. This was further confirmed by using a fluorescence tagged version of H-Ras (CFP-Ras =H-Ras tagged on its amino terminus with the cyan fluorescent protein); EGF induced a redistribution of CFP-Ras such that fluorescence disappeared for the plasma membrane and accumulated a punctate intracellular staining. Thus, it was conceivable that the anti-LeY antibodies exerted their inhibitory action on MAPK because they affected the intracellular routing of EGF-receptors. This was addressed by measuring the rates of internalization and of recycling in the absence and presence of anti-LeY antibodies. SKBR-3-cells were incubated with [$^{125}$I]EGF at 4° C. Unbound ligand was removed and internalization was initiated by warming the samples to 37° C. We measured the time-dependent change in surface-bound (i.e. acid-released) radioligand and in internalized (i.e. acid-resistant) radioligand binding. Surface bound ligand disappeared with a rapid monoexponential decay ($k_{int}$=0.39±0.07 min$^{-1}$) which was reasonably similar to the rate determined for the appearance of internalized receptors (=0.24±0.06 min$^{-1}$); however, the monoclonal antibodies did not cause a consistent change in these rates (data not shown). We therefore characterized recycling by allowing SKBR-3-cells to internalize [$^{125}$I]EGF during a preincubation at 37° C. Subsequently, the unbound ligand was removed and the cells were held at 4° C. Thereafter, the internalized [$^{125}$I]EGF was allowed to recycle to the surface in fresh medium at 37° C. We determined time course of the reappearance of [$^{125}$I]EGF in the medium, which is indicative of receptors recycling to the cell surface. ABL364 and IGN311 caused an increase of a readily exchanging pool compared to control conditions. As expected for steady state conditions (see also FIG. 5B), the membrane-bound fraction of [$^{125}$I]EGF (i.e. the acid-sensitive fraction) remained constant and it was comparable in ABL364-treated cells and control cells. The data suggest that in the presence of ABL364 and IGN311, EGF-receptor containing endosomes are shifted into a compartment that allows for more rapid recycling. To visualize this shift, we studied the distribution pattern of fluorescent EGF. SKBR-3 cells, grown on cover slips were incubated with 20 nM Oregon-Green-labeled EGF in the absence or presence of ABL364, of IGN311. It was shown in fluorescence microscopy that in the presence of ABL364 and IGN311, the distribution pattern of the fluorescent EGF differs from that under control conditions. Under control conditions, the fluorescence shows a disperse punctate pattern, whereas in the presence of ABL364 and IGN311 the fluorescent EGF is clustered in a submembrane compartment. We verified that this fluorescence staining was indeed intracellular by determining the effect of an acid strip. This manipulation did neither affect the staining pattern in the presence of IGN311 nor of ABL364 (data not shown). Finally, as an additional control, we incubated cells with trastuzumab which did not alter the distributions pattern of fluorescent EGF. This fits to the observation that neither the internalization (not shown) nor the recycling kinetics were altered by the addition of trastuzumab.

The invention claimed is:

1. A method of treating a patient to reduce or inhibit the growth of tumor cells in a cancer by inhibiting glycosylated tumor cell receptors comprising administering to a patient an antibody directed against a tumor-cell receptor associated glycosylation antigen, wherein said antibody inhibits MAPK activation in said tumor cells and thereby inhibits activated MAPK mediated cell division, and wherein said antibody does not inhibit said glycosylated receptor from binding to its ligand.

2. The method according to claim 1, further comprising chemotherapy treatment of said patient.

3. The method according to claim 1, wherein the tumor cells of said patient are resistant to chemotherapy.

4. The method according to claim 1, wherein said antibodies are administered for treating a minimal residual disease.

5. The method according to claim 1, wherein said antibodies inhibit a mitogenic stimulation of said tumor cells by the epidermal growth factor (EGF) and/or by heregulin.

6. The method according to claim 1, wherein said tumor cells express a receptor from the family of the EGF receptors, and wherein said antibodies promote a lysis of said tumor cells.

7. The method according to claim 1, wherein said antibody is directed against Lewis antigens.

8. The method according to claim 1, wherein said antibody is directed against an aberrant glycosylation.

9. The method according to claim 8, wherein said aberrant glycosylation is a Lewis x-, Lewis b- or Lewis-y-structure, sialyl-Tn, Tn antigen, GloboH, KH1, TF antigen or an alpha-1,3-galactosyl epitope.

10. The method according to claim 1, wherein said antibody is a monoclonal antibody.

11. The method according to claim 10, wherein said monoclonal antibody is a human, humanized, chimeric or murine antibody.

12. The method according to claim 1, wherein said antibody has an affinity to binding the EGF receptor with a dissociation constant of below a Kd value of $10^{-6}$ mol/l, or less is used.

13. The method according to claim 1, wherein said antibody is used in a dose of at least 50 mg.

14. The method according to claim 1, wherein said antibody is an antibody derivative which comprises at least the Fab-portion of an antibody and binds to a tumor-associated glycosylation.

15. The method according to claim 1, wherein said patient suffers from a cancer with tumor cells which express a receptor from the family of the EGF receptors.

16. The method according to claim 1, wherein a body fluid or a tissue from a cancer patient is treated ex vivo.

17. The method according to claim 16, wherein the cancer patient is treated within the frame of a high dosage chemotherapy.

18. The method according to claim 16, wherein the body fluid, or the tissue, respectively, is derived from a patient at risk for a cancer disease.

19. The method according to claim 1, wherein said antibody is a humanized antibody directed against Lewis Y antigen.

20. The method according to claim 19, wherein said antibody is administered in combination with a carrier.

21. The method of claim 12, wherein said Kd value is less than $10^{-7}$ mol/l.

22. The method of claim 12, where said Kd is less than $10^{-8}$ mol/l.

23. The method of claim 13, said dose is at least 100 mg and up to 2 g per patient.

24. The method of claim 13, wherein said dose at least 200 mg and up to 2 g per patient.

25. The method of claim 16, wherein said body fluid or said tissue is selected from the group consisting of an organ, bone marrow, blood and serum.

26. The method of claim 13, wherein said antibody is used at a dose of at least 100 mg per patient.

27. The method of claim 13, wherein said antibody is used at a dose of at least 200 mg, per patient.

28. The method of claim 13, wherein said antibody is used at a dose of at least 100 mg, per patient.

* * * * *